US010517589B2

(12) United States Patent
Kostrzewski

(10) Patent No.: US 10,517,589 B2
(45) Date of Patent: Dec. 31, 2019

(54) SURGICAL STAPLES WITH EXPANDABLE BACKSPAN

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 230 days.

(21) Appl. No.: 15/808,203

(22) Filed: Nov. 9, 2017

(65) Prior Publication Data

US 2018/0317908 A1 Nov. 8, 2018

Related U.S. Application Data

(63) Continuation-in-part of application No. 15/587,747, filed on May 5, 2017.

(51) Int. Cl.
*A61B 17/068* (2006.01)
*A61B 17/064* (2006.01)
(Continued)

(52) U.S. Cl.
CPC .... *A61B 17/0644* (2013.01); *A61B 17/07207* (2013.01); *A61B 17/068* (2013.01);
(Continued)

(58) Field of Classification Search
CPC . A61B 17/068; A61B 17/064; A61B 17/0644; A61B 17/0682; A61B 17/0684;
(Continued)

(56) References Cited

U.S. PATENT DOCUMENTS

| 3,079,606 A | 3/1963 | Bobrov et al. |
| 3,490,675 A | 1/1970 | Green et al. |
| (Continued) | | |

FOREIGN PATENT DOCUMENTS

| AU | 198654765 | 9/1986 |
| CA | 2773414 A1 | 11/2012 |
| (Continued) | | |

OTHER PUBLICATIONS

European Search Report dated Dec. 21, 2018, issued in EP Appln. No. 18170882.

(Continued)

*Primary Examiner* — Scott A Smith
(74) *Attorney, Agent, or Firm* — Carter, DeLuca & Farrell LLP

(57) ABSTRACT

A surgical staple includes a body includes a first leg, a second leg, and a backspan. The backspan has a first portion, a second portion, a third portion, and a crimped region. The first portion of the backspan includes a looped member. The second portion of the backspan extends between a first end portion of the first leg and a first end portion of the looped member. The third portion of the backspan extends between a first end portion of the second leg and a second end portion of the looped member. The crimped region includes a crimped section in at least one of the second portion or the third portion of the backspan. A combined wire thickness of the second and third portions of the backspan in the crimped region is about equal to the diameter of the body of the surgical staple.

20 Claims, 12 Drawing Sheets

(51) Int. Cl.
*A61B 17/072* (2006.01)
*A61B 17/00* (2006.01)

(52) U.S. Cl.
CPC ... A61B 17/072 (2013.01); A61B 2017/00398
(2013.01); A61B 2017/00473 (2013.01); A61B
2017/00862 (2013.01); A61B 2017/00884
(2013.01); A61B 2017/00893 (2013.01); A61B
2017/0725 (2013.01); A61B 2017/07228
(2013.01); A61B 2017/07235 (2013.01); A61B
2017/07242 (2013.01); A61B 2017/07264
(2013.01); A61B 2017/07271 (2013.01); A61B
2017/07278 (2013.01); A61B 2017/07285
(2013.01)

(58) Field of Classification Search
CPC ............ A61B 17/072; A61B 17/07207; A61B
17/115; A61B 17/07292; A61B
2017/07271; A61B 2017/00668; A61B
2017/07228; A61B 2017/07242; A61B
2017/00893
USPC ................ 227/19, 175.1, 176.1, 902, 180.1;
606/139, 153, 151, 75, 213, 219;
411/457, 920
See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,364,406 A * | 11/1994 | Sewell, Jr. ......... A61B 17/0644 128/898 |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,413,584 A | 5/1995 | Schulze |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |

(56) References Cited

U.S. PATENT DOCUMENTS

| | | |
|---|---|---|
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huiterna et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,976,159 A * | 11/1999 | Bolduc ............ A61B 17/064 606/104 |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |

(56) References Cited

U.S. PATENT DOCUMENTS

| | | |
|---|---|---|
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |

(56) References Cited

U.S. PATENT DOCUMENTS

| | | |
|---|---|---|
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |

(56) References Cited

U.S. PATENT DOCUMENTS

| | | |
|---|---|---|
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |

(56) References Cited

U.S. PATENT DOCUMENTS

| | | |
|---|---|---|
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |

(56) References Cited

U.S. PATENT DOCUMENTS

| | | |
|---|---|---|
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |

(56) References Cited

U.S. PATENT DOCUMENTS

| | | |
|---|---|---|
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty |
| 9,386,983 B2 | 7/2016 | Swensgard et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Ohakad et al. |
| 9,549,735 B2 | 1/2017 | Shelton, IV et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0034953 A1 | 2/2011 | Milo |
| 2011/0036891 A1 | 2/2011 | Zemlok et al. |
| 2011/0042439 A1* | 2/2011 | Johnson .......... A61B 17/0644 227/175.1 |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |

(56) References Cited

U.S. PATENT DOCUMENTS

| | | |
|---|---|---|
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |

(56) References Cited

U.S. PATENT DOCUMENTS

| | | |
|---|---|---|
| 2015/0209040 A1 | 7/2015 | Whitman et al. |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi |
| 2016/0249915 A1 | 9/2016 | Beckman et al. |
| 2016/0249916 A1 | 9/2016 | Shelton, IV et al. |
| 2016/0249924 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0 760 230 A1 | 3/1997 |
| EP | 1728473 A1 | 12/2006 |
| EP | 1952769 A2 | 8/2008 |
| EP | 2090253 A2 | 8/2009 |
| EP | 2090254 A1 | 8/2009 |
| EP | 2286735 A1 | 2/2011 |
| EP | 2583630 A2 | 4/2013 |
| EP | 2586382 A2 | 5/2013 |
| EP | 2907456 A1 | 8/2015 |
| EP | 3257448 A2 | 12/2017 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51-149985 | 12/1976 |
| JP | 2001-87272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 08302247 | 7/1983 |
| WO | 8904146 A1 | 5/1989 |
| WO | 89/10094 A1 | 11/1989 |

(56) References Cited

FOREIGN PATENT DOCUMENTS

| WO | 9210976 | A1 | 7/1992 |
| WO | 9308754 | A1 | 5/1993 |
| WO | 9314706 | A1 | 8/1993 |
| WO | 2004/032760 | A2 | 4/2004 |
| WO | 2009071070 | A2 | 6/2009 |
| WO | 2011153408 | A1 | 12/2011 |
| WO | 2012031204 | A2 | 3/2012 |
| WO | 20150191887 | A1 | 12/2015 |

OTHER PUBLICATIONS

European Search Report dated Mar. 21, 2019, issued in EP Appln. No. 18205075.

\* cited by examiner

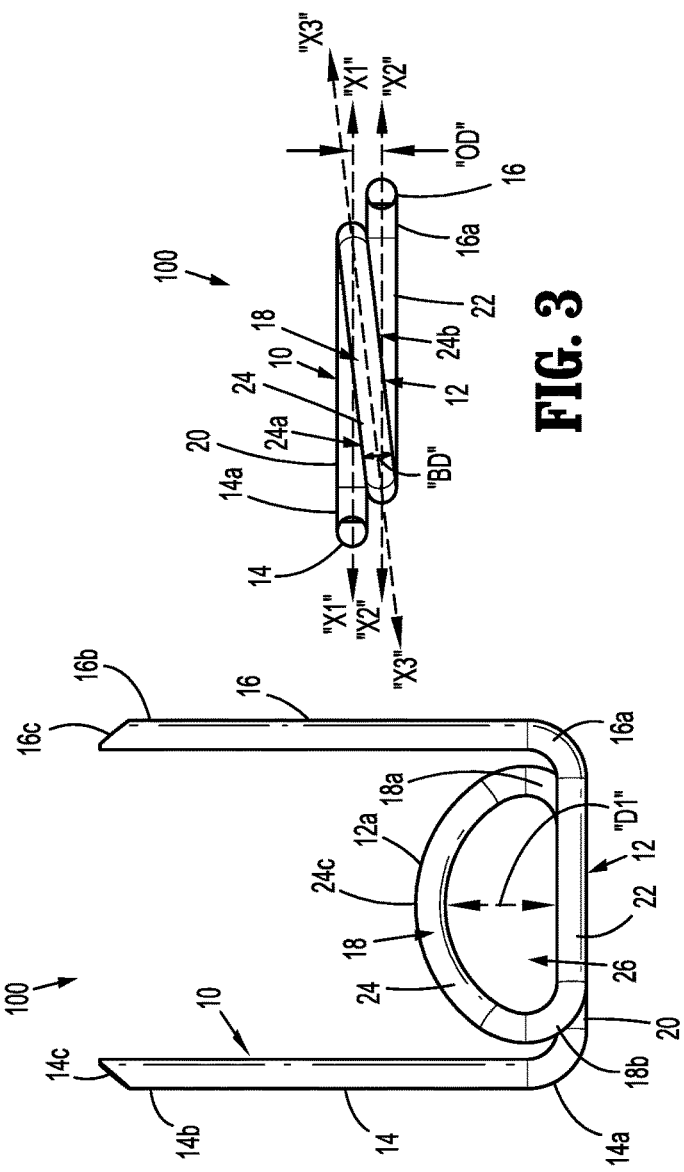

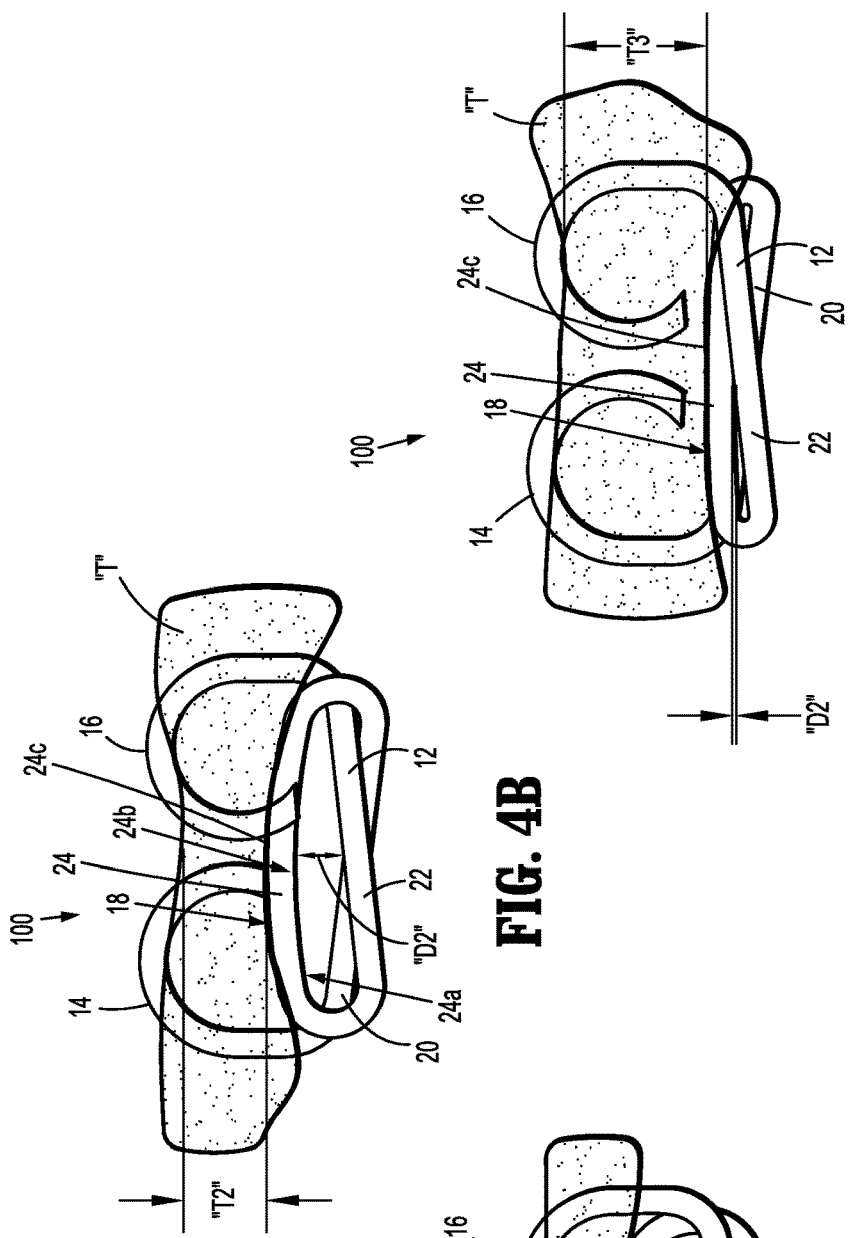

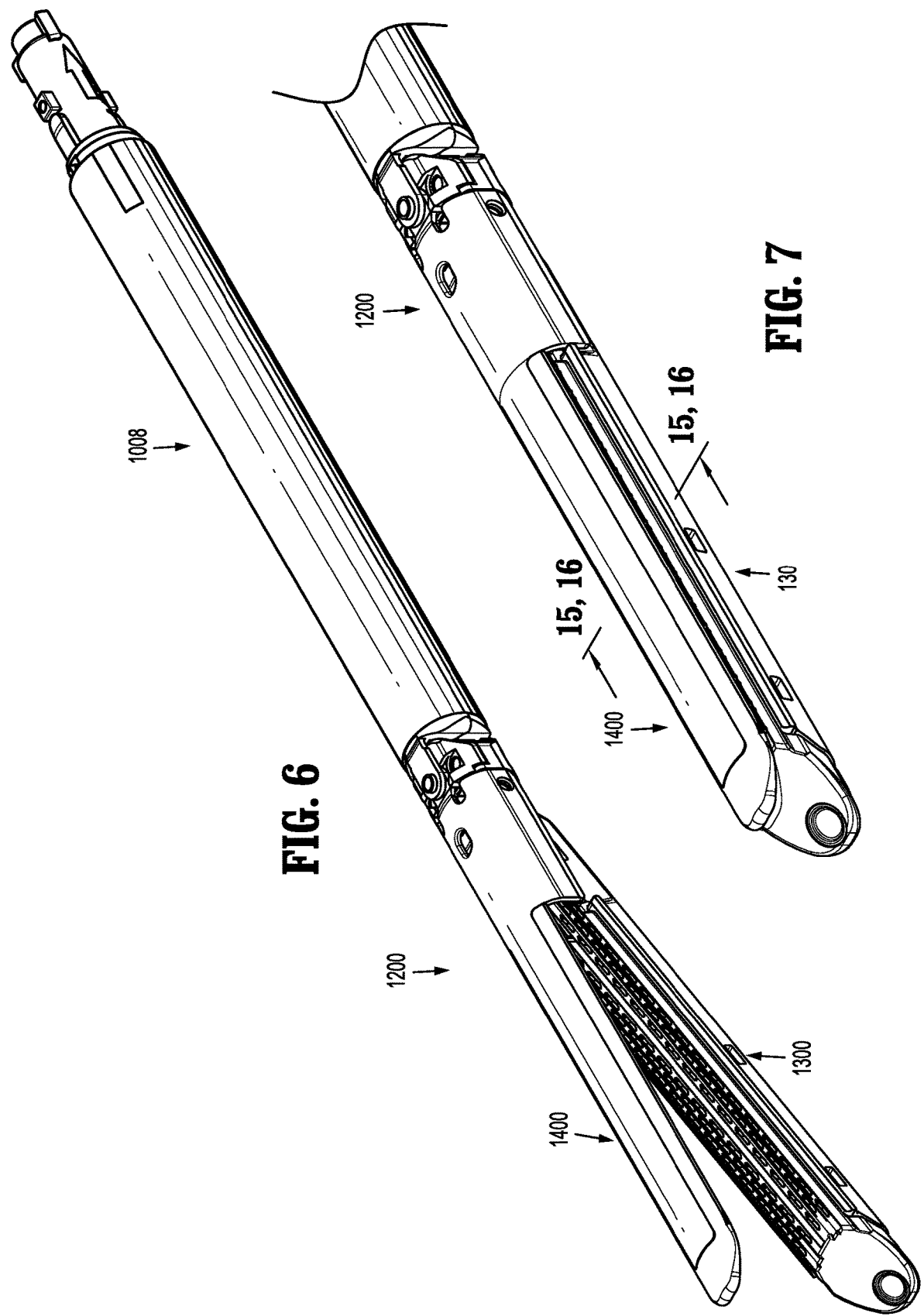

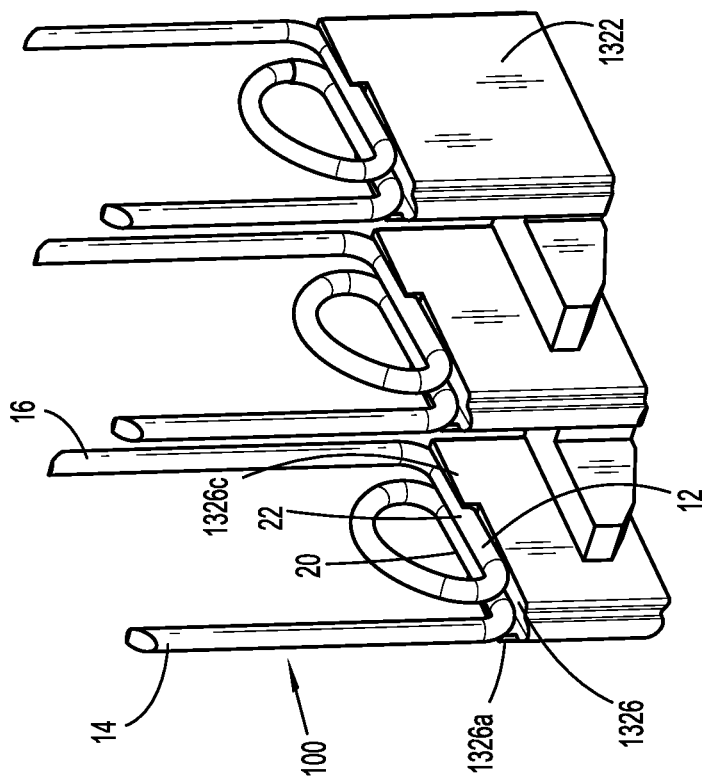
FIG. 13
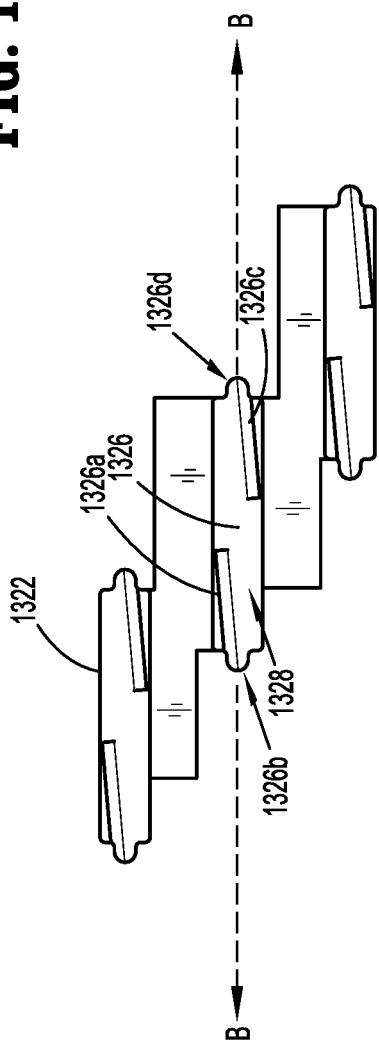
FIG. 12
FIG. 14

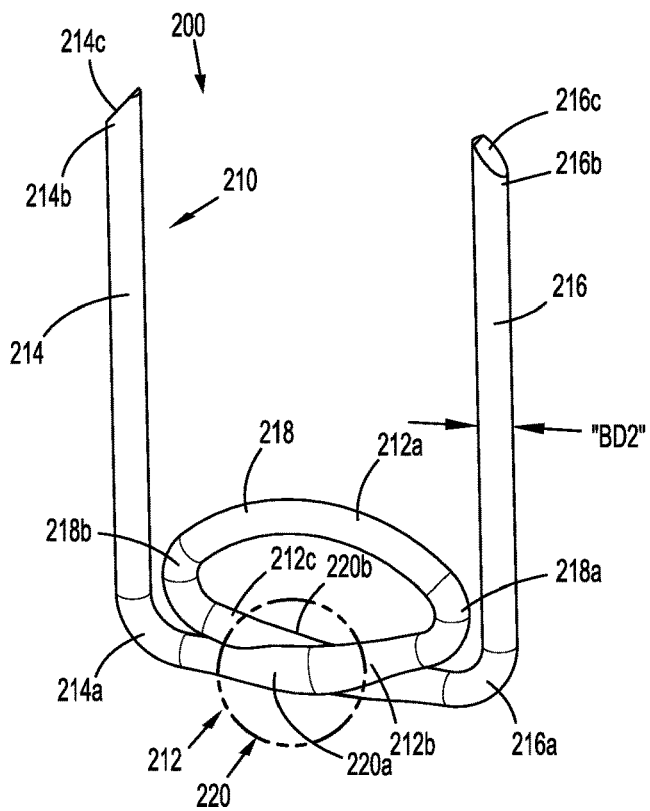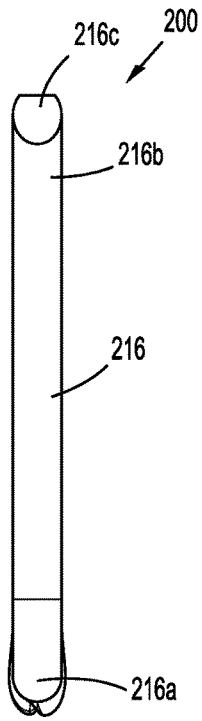
FIG. 17A  FIG. 17D
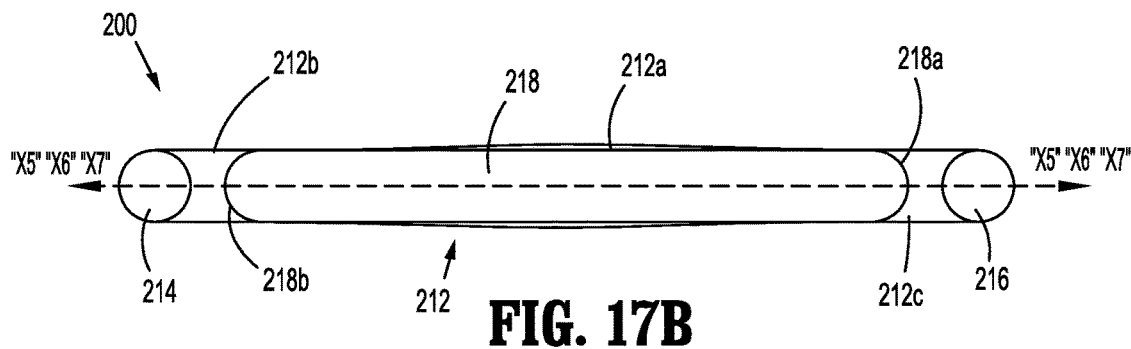
FIG. 17B
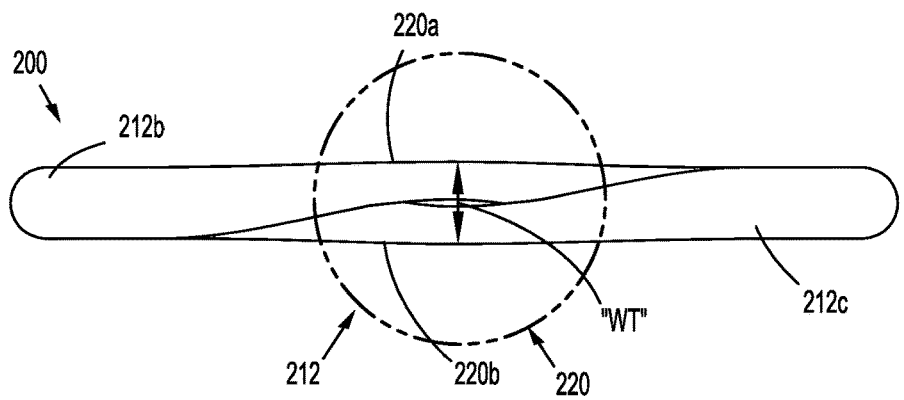
FIG. 17C

SURGICAL STAPLES WITH EXPANDABLE BACKSPAN

CROSS-REFERENCE TO RELATED APPLICATION

This application is a continuation in part of U.S. patent application Ser. No. 15/587,747 filed May 5, 2017, and the disclosure of the above-identified application is hereby incorporated by reference in its entirety.

BACKGROUND

1. Technical Field

The present disclosure relates to surgical staples for use with surgical stapling instruments. More particularly, the present disclosure relates to surgical staples for use with surgical stapling instruments for joining tissue of varying thicknesses.

2. Background of Related Art

Surgical staples are applied to tissue using surgical stapling instruments to join tissue or tissue segments in a fast and efficient manner in a variety of surgical procedures, e.g., anastomoses procedures.

Typically, a surgical staple includes a backspan and a pair of spaced legs. The legs are driven through tissue and into an anvil assembly of a surgical stapling instrument to deform the staple into a desired configuration, e.g., B-staple, to effect hemostasis. Current surgical staples are particularly sized and suited for tissue of a given thickness range to effect hemostasis. As such, a clinician must choose a staple having an appropriate size for a given tissue thickness range to ensure effective hemostasis. If the tissue thickness is misidentified by the clinician or if the tissue thickness falls near the outer edges of the range for a given staple size, the likelihood of ineffective hemostasis is increased.

Accordingly, a continuing need exists in the suturing arts for a surgical staple that is capable of accommodating a greater range of tissue thicknesses to provide the clinician greater flexibility when performing a variety of surgical procedures.

SUMMARY

The present disclosure provides in one aspect a surgical staple including a body having a diameter and including a first leg, a second leg, and a backspan. The first and second legs each have a first end portion and a second end portion. The backspan has a first portion, a second portion, a third portion, and a crimped region. The first portion of the backspan includes a looped member having a first end portion and a second end portion. The second portion of the backspan extends between the first end portion of the first leg and the first end portion of the looped member. The third portion of the backspan extends between the first end portion of the second leg and the second end portion of the looped member. The crimped region includes a crimped section defined in at least one of the second portion or the third portion of the backspan. A combined wire thickness of the second and third portions of the backspan in the crimped region is about equal to the diameter of the body of the surgical staple.

In certain embodiments, the crimped region of the backspan includes a first crimped section defined on the second portion of the backspan and a second crimped section defined on the third portion of the backspan. In such embodiments, the combined wire thickness of the crimped region is about equal to the diameter of the body of the surgical staple.

In some embodiments, first crimped section of the second portion of the backspan overlaps with the second crimped section of the third portion of the backspan.

In certain embodiments, the first crimped section of the second portion of the backspan is axially aligned with the second crimped section of the third portion of the backspan.

In some embodiments, the looped member of the backspan defines a first axis that extends between the first end portion of the looped member and the second end portion of the looped member.

In certain embodiments, the second portion of the backspan defines a second axis and the third portion of the backspan defines a third axis. In such embodiments, the first axis of the looped member is parallel with the second axis of the second portion and the third axis of the third portion.

In some embodiments, the second axis of the second portion of the backspan is laterally aligned with the third axis of the third portion of the backspan such that the first leg and the second leg of the surgical staple are axially aligned.

In certain embodiments, the looped member of the backspan includes an apex, the second portion of the backspan includes a first mid-portion, and the third portion of the backspan includes a second mid-portion. In such embodiments, the apex of the looped member and the first and second mid-portions of the second and third portions of the backspan define an axis that is perpendicular to the second axis of the second portion of the backspan and the third axis of the third portion of the backspan.

In some embodiments, the surgical staple includes an unformed configuration and a formed configuration. In the unformed configuration of the surgical staple, the apex of the looped member of the backspan is spaced apart from each of the second and third portions of the backspan a first distance. In the formed configuration of the surgical staple, the apex of the looped member of the backspan is spaced apart from each of the second and third portions of the backspan a second distance that is less than the first distance.

In some embodiments, the backspan of the surgical staple is positioned to engage tissue such that the second distance between the apex of the looped member of the backspan and each of the second and third portions of the backspan decreases as a thickness of tissue engaged by the backspan increases.

In certain embodiments, in the formed configuration of the surgical staple, the first leg of the surgical staple is positioned on a first lateral side of the looped member and the second leg of the surgical staple is positioned on a second lateral side of the looped member opposite the first lateral side of the looped member.

The present disclosure provides in another aspect a surgical staple including a body having a first leg, a second leg, and a backspan. The first and second legs each have a first end portion and a second end portion. The backspan has a first portion, a second portion, a third portion, and a crimped region. The first portion of the backspan has a first end portion and a second end portion. The second portion of the backspan extends longitudinally between the first end portion of the first leg and the first end portion of the first portion. The second portion defines a first axis. The third portion of the backspan extends longitudinally between the first end portion of the second leg and the second end portion of the first portion. The third portion defines a second axis.

The crimped region includes a crimped section defined in at least one of the second portion or the third portion of the backspan. The crimped region aligns the first axis of the second portion with the second axis of the third portion.

In some embodiments, the first portion includes a looped member positioned between the first end portion and the second end portion of the first portion of the backspan.

In certain embodiments, the looped member of the first portion of the backspan defines a third axis that is parallel with the first axis of the second portion of the backspan and the second axis of the third portion of the backspan.

In some embodiments, in the crimped region, the second and third portions of the backspan include a combined wire thickness that is about equal to a diameter of the body of the surgical staple.

In some embodiments, the crimped section defined in the at least one of the second portion or the third portion of the backspan axially aligns the first end portion of the first leg with the first end portion of the second leg.

In certain embodiments, the crimped region of the backspan is disposed between the first end portion of the first leg and the first end portion of the second leg.

In certain embodiments, the second portion of the backspan and the third portion of the backspan are in lateral contact.

BRIEF DESCRIPTION OF THE DRAWINGS

Various embodiments of the presently disclosed expandable backspan staples and cartridges for supporting the staples are disclosed herein with reference to the drawings, wherein:

FIG. 1 is a perspective view of an exemplary embodiment of the presently disclosed surgical staple, illustrating the surgical staple in a unformed configuration;

FIG. 2 is a front view of the surgical staple of FIG. 1;

FIG. 3 is a top view of the surgical staple of FIG. 1;

FIG. 4A is a front view of the surgical staple of FIG. 1 in a formed configuration engaging tissue having a first thickness;

FIG. 4B is a front view of the surgical staple of FIG. 1 in the formed configuration engaging tissue having a second larger thickness;

FIG. 4C is a front view of the surgical staple of FIG. 1 in the formed configuration engaging tissue having a third even larger thickness;

FIG. 6 is a perspective view of a loading unit of the surgical stapling instrument of FIG. 5 with the tool assembly of the loading unit in the unclamped position;

FIG. 7 is a perspective view of the tool assembly of FIG. 6 in the clamped position;

FIG. 12 is a side, perspective view of a pusher of the staple cartridge assembly of FIG. 8;

FIG. 13 is a side, perspective view of the pusher of FIG. 12 with a plurality the surgical staples of FIG. 1 disposed on the pusher;

FIG. 14 is a top view of the pusher of FIG. 12;

FIG. 17A is a perspective view of an exemplary embodiment of a surgical staple in accordance with another aspect of the present disclosure, illustrating the surgical staple in a unformed configuration;

FIG. 17B is a top view of the surgical staple of FIG. 17A;

FIG. 17C is a bottom view of the surgical staple of FIG. 17A;

FIG. 17D is a side view of the surgical staple of FIG. 17A;

DETAILED DESCRIPTION OF EMBODIMENTS

Figure 5:
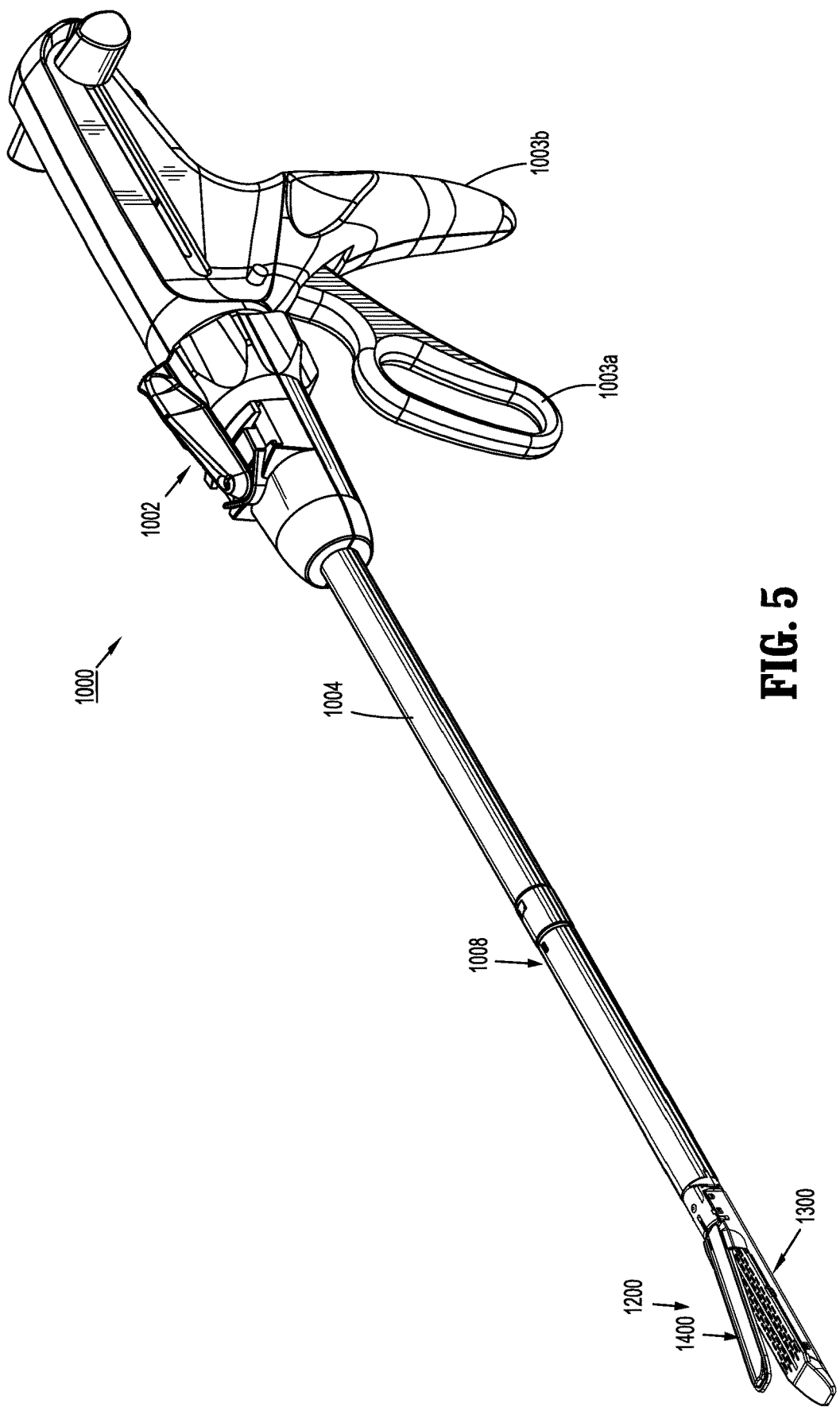
FIG. 5 is a perspective view of a surgical stapling instrument including a cartridge that supports the surgical staples of FIG. 1 with a tool assembly of the surgical stapling instrument in an unclamped position.

Embodiments of the presently disclosed surgical staple will now be described in detail with reference to the drawings wherein like references numerals identify similar or identical elements. In the drawings, and in the following description, the term "proximal" should be understood to refer to that portion or end of the instrument that is closest to a user during proper use, while the term "distal" should be understood to refer to that portion or end of the instrument that is furthest from a user during proper use, as is traditional and conventional in the art. Also, as used in the specification, the terms "approximately equal," "substantially equal," and "about equal" should be understood to include +/−15% of a given parameter.

Referring initially to FIGS. 1-3, an exemplary embodiment of the present disclosure is shown generally as a surgical staple 100. The surgical staple 100 includes a body 10 having a backspan 12, a first leg 14, and a second leg 16. The surgical staple 100 has an unformed configuration, as shown in FIGS. 1-3, wherein the first leg 14 and the second leg 16 are parallel, or substantially parallel, to one another and spaced a distance from one another. Alternatively, in the unformed configuration, the first and second legs 14, 16 can diverge slightly or converge slightly, etc. in relation to each other.

Each of the first and second legs 14, 16 includes a first end portion 14a, 16a, respectively, and a second end portion 14b, 16b, respectively. Each of the second end portions 14b, 16b of the first and second legs 14, 16 includes a tissue-penetrating tip 14c, 16c. In one embodiment, each of the tissue-penetrating tips 14c, 16c of the respective first and second legs 14, 16 of the surgical staple 100 can be formed with beveled or tapered end to facilitate penetration of the first and second legs 14, 16 into tissue "T" (see FIGS. 4A-4C). Alternately, the tissue penetrating tips 14c, 16c of the respective first and second legs 14, 16 of the surgical staple 100 need not be tapered, can be tapered in a different direction, or can define a conical or flat surface.

With continued reference to FIGS. 1-3, the backspan 12 includes a first portion 12a having a looped member 18, a second portion 20 that is substantially linear and extends between the first end portion 14a of the first leg 14 and a first end portion 18a of the looped member 18, and a third portion 22 that is substantially linear and extends between the first end portion 16a of the second leg 16 and a second end portion 18b of the looped member 18. The looped member 18 of the backspan 12 includes an arcuate portion 24 that extends between the second and third portions 20, 22 of the backspan 12. In the unformed configuration of the surgical staple 100, the second portion 20 of the backspan 12 may be substantially parallel to the third portion 22 of the backspan 12 and in lateral contact or close alignment with the third portion 22 of the backspan 12, as illustrated in FIG. 1.

In embodiments, the arcuate portion 24 of the looped member 18 extends transversely between the second portion 20 and the third portion 22 of the backspan 12. In the unformed configuration of the surgical staple 100, the second portion 20 of the backspan 12 defines an axis "X1-X1" and the third portion 22 of the backspan 12 defines an axis "X2-X2". The axis "X1-X1" of the second portion 20 and the axis "X2-X2" of the third portion 22 may be laterally offset from each other an offset distance "OD". It is envisioned that the offset distance "OD" between the axis "X1-X1" of the second portion 20 and the axis "X2-X2" of the third portion 22 may be substantially equal to a diameter "BD" of the body 10 of the surgical staple 100 such that the second portion 20 and the third portion 22 are closely positioned or in contact with each other.

The arcuate portion 24 of the looped member 18 defines an axis "X3-X3" that extends between a first end portion 20a of the second portion 20 of the backspan 12 and a first end portion 22a of the third end portion 22 of the backspan 12. In embodiments, the looped member 18 and the second and third portions 20, 22 may define an enclosed opening 26 which may have a circular or oval configuration. It is envisioned that the arcuate portion 24 of the looped member 18 of the backspan 12 can be formed having any desired radius of curvature to suit a particular need, surgical procedure, or range of tissue thicknesses (as will be discussed below). It is also envisioned that the opening 26 defined by the backspan 12 need not be circular or oval but rather may have other configurations, such as, for example, U-shaped, trapezoidal, rectangular, etc. The backspan can have other shapes, such as round, rectilinear, etc., and the member 18 can be straight, angled or curved. Further, in embodiments, the backspan 12 may include more than one looped member 18.

The body 10 of the surgical staple 100 can have a circular cross-section throughout its length. Alternatively, it is envisioned that the body 10 of the surgical staple 100 may have a variety of different cross-sectional shapes including rectangular, oval, square, triangular, trapezoidal, etc. It is also envisioned that the backspan 12 of the surgical staple 100 and the first and second legs 14, 16 of the surgical staple 100 may have different cross-sectional shapes. For example, in one embodiment, the backspan 12 of the surgical staple 100 can have a rectangular cross-sectional shape and the first and second legs 14, 16 of the surgical staple 100 can have an oval cross-sectional shape.

The surgical staple 100 may be fabricated from a formable material, such as, for example, titanium, stainless steel or a variety of different bio-compatible polymers. In this manner, the surgical staple 100 may be introduced over tissue while in an unformed configuration, and then deformed or fastened onto the tissue to secure the surgical staple 100 to the tissue.

It is contemplated that the surgical staple 100 may be fabricated from any non-degradable, biocompatible material known by those having skill in the art.

Referring now to FIGS. 4A-4C, in some embodiments, the first and second legs 14, 16 of the surgical staple 100 are deformed against an anvil assembly 1400 (see FIG. 5) of a surgical stapling instrument 1000 into a substantially B-shaped staple configuration. Since the first and second legs 14, 16 of the surgical staple 100 extend from the second and third portions 20, 22 of the backspan 12, respectively, and the axis "X1-X1" of the second portion 20 and the axis "X2-X2" of the third portion 22 are laterally offset from each other by the offset distance "OD," which is substantially equal to the diameter "BD" of the body 10 of the surgical staple 100, it is envisioned that in the formed configuration of the surgical staple 100, the first leg 14 of the surgical staple 100 is positioned on a first lateral side 24a of the arcuate portion 24 of the looped member 18 and the second leg 16 is positioned on a second, opposite lateral side 24b of the arcuate portion 24 of the looped member 18 (see FIGS. 3, 4A, and 4B).

In the formed configuration, the arcuate portion 24 of the looped member 18 of the backspan 12 is configured to deform relative to the second and third portions 20, 22 of the backspan 12, wherein the first and second transverse portions 20, 22 of the looped member 18 of the backspan 12 remain substantially linear. Specifically, the deformation of the backspan 12 of the surgical staple 100 is dependent upon a thickness, e.g., "T1," "T2," "T3," etc., of the tissue "T" to be fastened. Initially, in the unformed configuration of the surgical staple 100, the looped member 18 of the backspan 12 includes an uncompressed distance "D1" between an apex 24c of the arcuate portion 24 of the looped member 18 and the second and third portions 20, 22 of the backspan 12, as illustrated in FIG. 2. In some embodiments, it is contemplated that the apex 24c of the arcuate portion 24 and a mid-portion "M1" (see FIG. 1) of the second portion 20 of the backspan 12 and a mid-portion "M2" (see FIG. 1) of the third portion 22 of the backspan 12 defines an axis "X4-X4" that is substantially parallel to at least one of the first and second legs 14, 16 of the surgical staple 100 and/or substantially perpendicular to the axis "X1-X1" of the second portion 20 of the backspan 12 and the axis "X2-X2" of the third portion 22 of the backspan 12. Upon engagement with the tissue "T," the looped member 18 of the backspan 12 is compressed between the tissue "T" and anvil assembly 1400 (see FIG. 5) of a surgical stapling instrument 1000 such that, the looped member 18 of the backspan 12 defines a compressed distance "D2" between the apex 24c of the arcuate portion 24 of the looped member 18 and the second and third portions 20, 22 of the backspan 12, as illustrated in FIGS. 4A-4C. As the looped member 18 contacts tissue "T" positioned between the first and second legs 14 and the looped member 18 as the staples 100 are deformed, the distance ""D2" decreases an amount that is directly related to the thickness of the tissue "T". More specifically, as the thickness of the tissue increases, the force applied to the looped member 18 by the tissue "T" positioned between the first and second legs 14, 16 and the looped member 18 of the staples 100 as the staples 100 are deformed increases, to increase the amount of deformation of the looped member 18.

FIG. 4A illustrates a staple 100 as the staple 100 is formed in relatively thin tissue "T" having a first thickness "T1". As the staple 100 is deformed about relatively thin tissue "T" having a thickness "T1", the tissue "T" is compressed between the first and second legs 14, 16 and the looped member 18 of the staples 100. As the first and second legs 14, 16 of the staple 100 are deformed into a B-configuration against the anvil assembly 1400 of the surgical stapling instrument 1000 (FIG. 5), the first and second legs 14, 16 push tissue "T" towards and against the looped member 18 of the backspan 12. Because the anvil assembly 1400 is disposed a fixed distance from the cartridge assembly 1300 when the stapling instrument is fired (as described in detail below), all of the tissue "T" must fit between the first and second legs 14, 16 and the looped member 18 of the backspan 12. Thus, where the tissue "T" is relatively thin, the tissue does not apply any substantial forces onto the looped member 18 as the first and second legs 14, 16 are deformed and little or no deformation to the looped member 18 occurs. Thus, the distance "D2" between the apex 24c of the arcuate portion 24 of the looped member 18 and the second and third portions 20, 22 of the surgical staples 100 remains substantially unchanged or only decreases slightly. Referring to FIG. 4B, where the tissue "T" has a moderate thickness of "T2", the tissue "T" requires more space between the first and second legs 14, 16 and the looped member 18 of the backspan 12. Thus, as the first and second legs 14, 16 are deformed against the anvil assembly 1400 and the tissue "T" is pushed towards the looped member 18 of the backspan 12, a greater force is applied to the looped member 18 to cause greater amount of deformation of the looped member 18 of the backspan 12. Thus, the distance "D2" between the apex 24c of the arcuate portion 24 of the looped member 18 and the second and third portions 20, 22 of the backspan 12 of the surgical staple 100 decreases a moderate amount. Similarly, where the tissue "T" has a large thickness of "T3" as shown in FIG. 4C, the tissue "T" requires even more space between the first and second legs 14, 16 and the looped member 18 of the backspan 12 as the staple 100 is deformed. Thus, as the first and second legs 14, 16 are deformed against the anvil assembly 1400 and the tissue "T" is pushed towards the looped member 18 of the backspan 12, an even greater force is applied to the looped member 18 to cause a greater amount of deformation of the looped member 18 of the backspan 12 to further reduce the distance D2" between the apex 24c of the arcuate portion 24 of the looped member 18 and the second and third portions 20, 22 of the backspan 12 of the surgical staple 100.

As illustrated in FIGS. 4A-4C, it is envisioned that the arcuate portion 24 of the looped member 18 of the backspan 12 becomes progressively more linear as the thickness of the tissue "T" increases. The ability of the backspan 12 of the surgical staple 100 to deform in accordance with the relative thickness of the tissue "T" facilitates the use of the presently disclosed staples with tissue having a wider range of thicknesses while providing effective hemostasis.

In order to place the presently disclosed surgical staple 100 in the tissue "T," a surgical apparatus in the form of the surgical stapling instrument 1000 is provided, as illustrated in FIG. 5. The surgical stapling instrument 1000 is approximated and fired similarly to, and in accordance with other known surgical stapling instrument, for example, the surgical stapling instrument disclosed in U.S. Pat. No. 5,865,361, the entire content of which is incorporated herein by reference.

As illustrated in FIG. 5, the surgical stapling instrument 1000 generally includes a handle assembly 1002 with a movable handle 1003a and a stationary handle 1003b, an elongated shaft 1004 extending distally from the handle assembly 1002, and a loading unit 1008 that is coupled to a distal portion of the elongated shaft 1004. In any of the embodiments disclosed herein, the handle assembly can include, or be attached to, one or more motors, or could be configured to work with a surgical robotic system.

Figure 8:
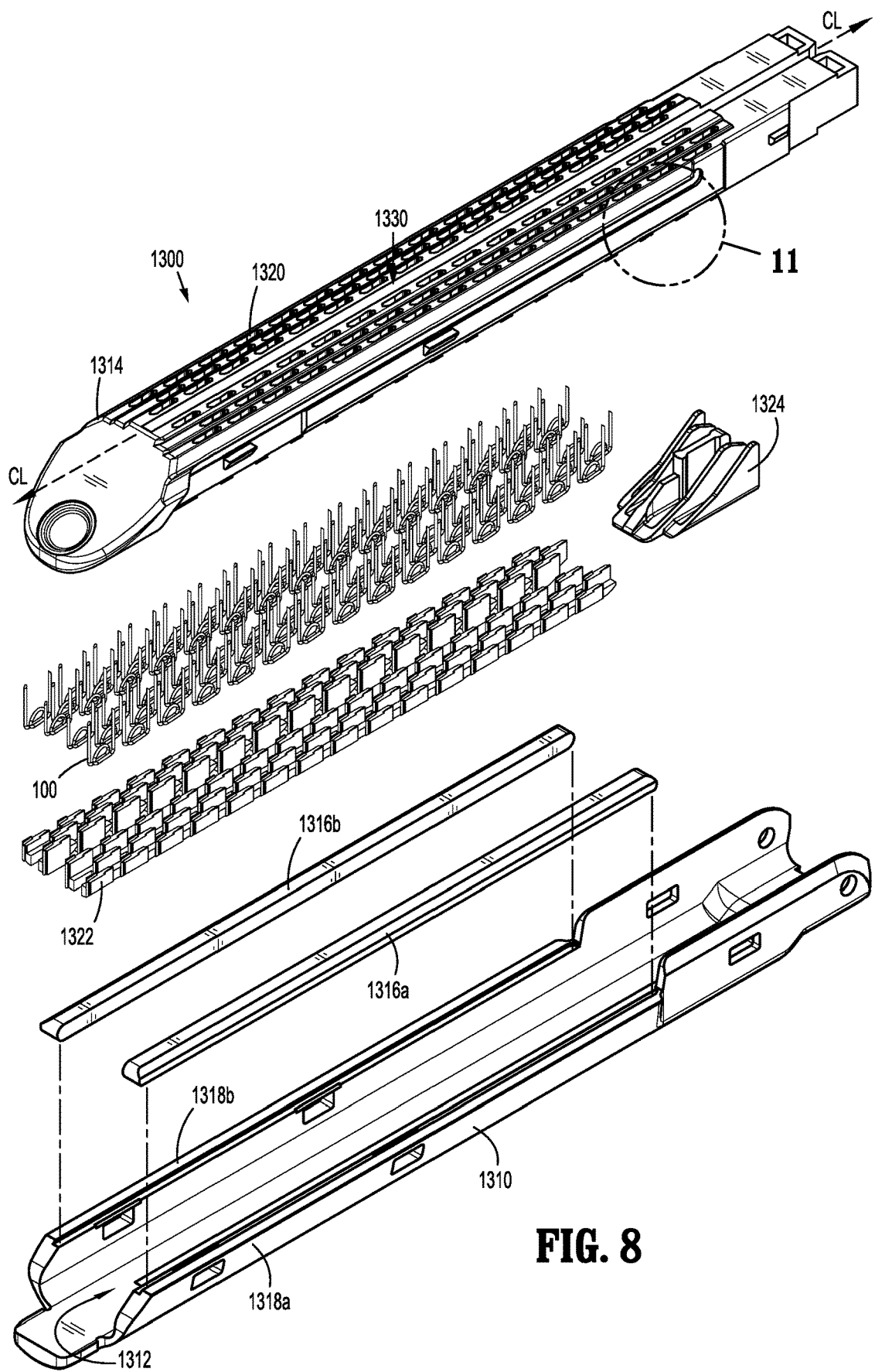
FIG. 8 is an exploded view of a staple cartridge assembly of the loading unit of FIG. 6.

With reference to FIGS. 6-8, the loading unit 1008 of the surgical stapling instrument 1000 includes a tool assembly 1200 having a staple cartridge assembly 1300 housing a plurality of surgical staples 100 (see FIG. 8) and an anvil assembly 1400 movably secured in relation to the staple cartridge assembly 1300 such that the tool assembly 1200 is movable between an open configuration (see FIG. 6) where the staple cartridge assembly 1300 is spaced apart from the anvil assembly 1400, and a clamped configuration (see FIG. 7) where the staple cartridge assembly 1300 and the anvil assembly 1400 are approximated. Alternately, the cartridge assembly 1300 can be movably supported in relation to the anvil assembly 1400.

Turning now to FIG. 8, the staple cartridge assembly 1300 includes a carrier 1310 having an elongated support channel 1312. The elongated support channel 1312 is dimensioned and configured to receive a staple cartridge 1314. The staple cartridge assembly 1300 includes a pair of elastic or resilient members 1316a, 1316b that are configured and dimensioned to apply and maintain a constant compressive force to the tissue "T" positioned between the staple cartridge assembly 1300 and the anvil assembly 1400 (see FIGS. 15 and 16) of the tool assembly 1200. In embodiments, the pair of elastic or resilient members 1316a, 1316b may be configured as two substantially parallel, elongate members that are positioned between the staple cartridge 1314 and a pair of shoulders 1318a, 1318b formed on the carrier 1310, respectively. The pair of elastic members 1316a, 1316b may be attached to, or otherwise disposed on, the pair of shoulders 1318a, 1318b of the carrier 1310, and may be fixedly or releasably attached thereto in alternative embodiments. The pair of elastic members 1316a, 1316b is configured to compress to accommodate tissues of different thicknesses between the cartridge assembly 1300 and the anvil assembly 1400. For a more detailed description of the construction and operation of an example of the pair of elastic members 1316a, 1316b, reference may be made to U.S. Pat. No. 8,152,041, the entire content of which is incorporated herein by reference.

The staple cartridge 1314 of the staple cartridge assembly 1300 includes a plurality of staple pockets 1320 that are arranged in rows. The plurality of staple pockets 1320 are dimensioned for receiving the plurality surgical staples 100 and a plurality of pushers 1322, as will be detailed below. The staple cartridge assembly 1300 includes an actuation sled 1324 movably supported with in the elongated support channel 1312 of the carrier 1310. During operation, the actuation sled 1324 is configured to advance along the elongated support channel 1312 of the carrier 1310 to sequentially contact the plurality of pushers 1322, such that the plurality of pushers 1322 are displaced within the plurality of staple pockets 1320 to eject the plurality of surgical staples 100 from the plurality of staple pockets 1320 towards the anvil assembly 1400.

As detailed above with reference to FIGS. 1-4C, the axis "X1-X1" of the second portion 20 of the backspan 12 and the axis "X2-X2" of the third portion 22 of the backspan 12" are laterally offset from each other by the offset distance "OD". In order to compensate for the laterally offset orientation of the backspan 12 of the surgical staple 100 and ensure that the first and second legs 14, 16 of each of the plurality of surgical staples 100 are longitudinally aligned relative to the other plurality of surgical staples 100 in a corresponding row of surgical staples 100, the plurality of staple pockets 1320 of the staple cartridge 1314 and a plurality of staple seats 1326 of the plurality of pushers 1322 are dimensioned and shaped as detailed below.

Figure 9:
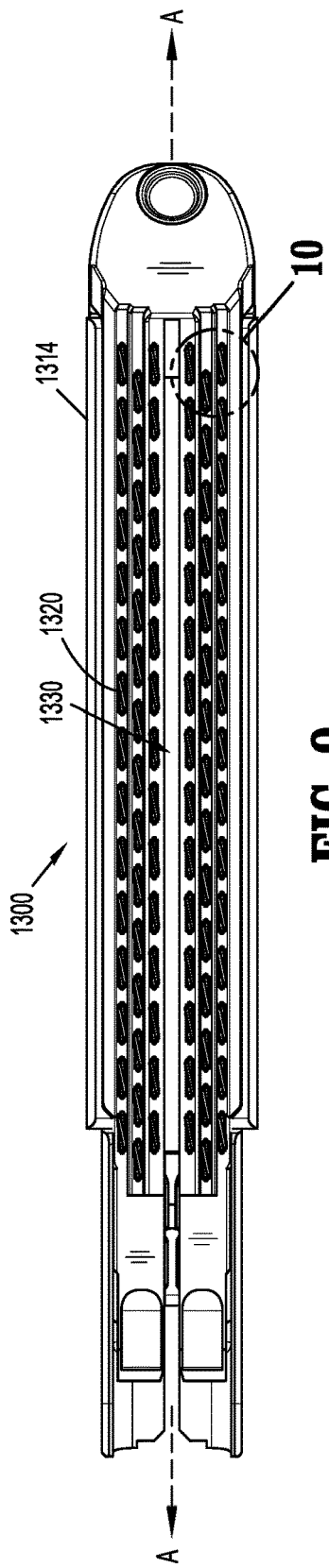
FIG. 9 is a top view of a staple cartridge of the staple cartridge assembly of FIG. 8.
Figure 11:
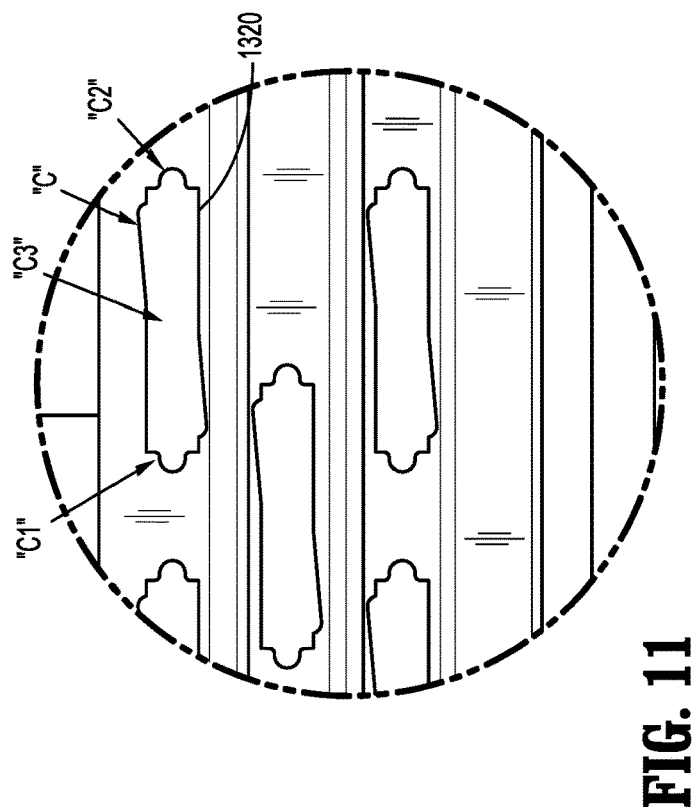
FIG. 11 is an enlarged view of the indicated area of detail delineated as 11 in FIG. 8.
Figure 10:
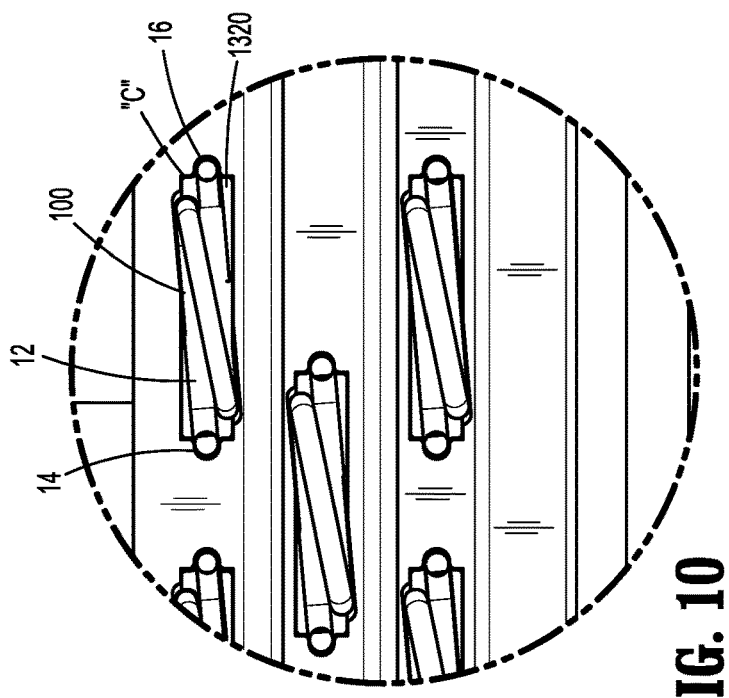
FIG. 10 is an enlarged view of the indicated area of detail delineated as 10 in FIG. 9.

Specifically, with reference to FIGS. 9-11, each of the plurality of staple pockets 1320 of the staple cartridge 1314 includes a contour "C" that corresponds to the orientation of the surgical staple 100 as shown in the top view of the surgical staple 100 in FIG. 3. The contour "C" of the staple pocket 1320 of the staple cartridge 1314 includes a first portion "C1" that is shaped and dimensioned to receive the first leg 14 of the surgical staple 100, a second portion "C2" that is shaped and dimensioned to receive the second leg 16 of the surgical staple 100, and an intermediate portion "C3" positioned between the first portion "C1" and the second portion "C2" that is shaped and dimensioned to receive the backspan 12 of the surgical staple 100. The plurality of staple pockets 1320 of the staple cartridge 1314 are skewingly positioned relative to a longitudinal axis "A-A" of the staple cartridge 1314 such that the first and second legs 14, 16 of each of the plurality of surgical staples 100 are longitudinally aligned relative to the other plurality of surgical staples 100 in the corresponding row of surgical staples 100.

Figure 16:
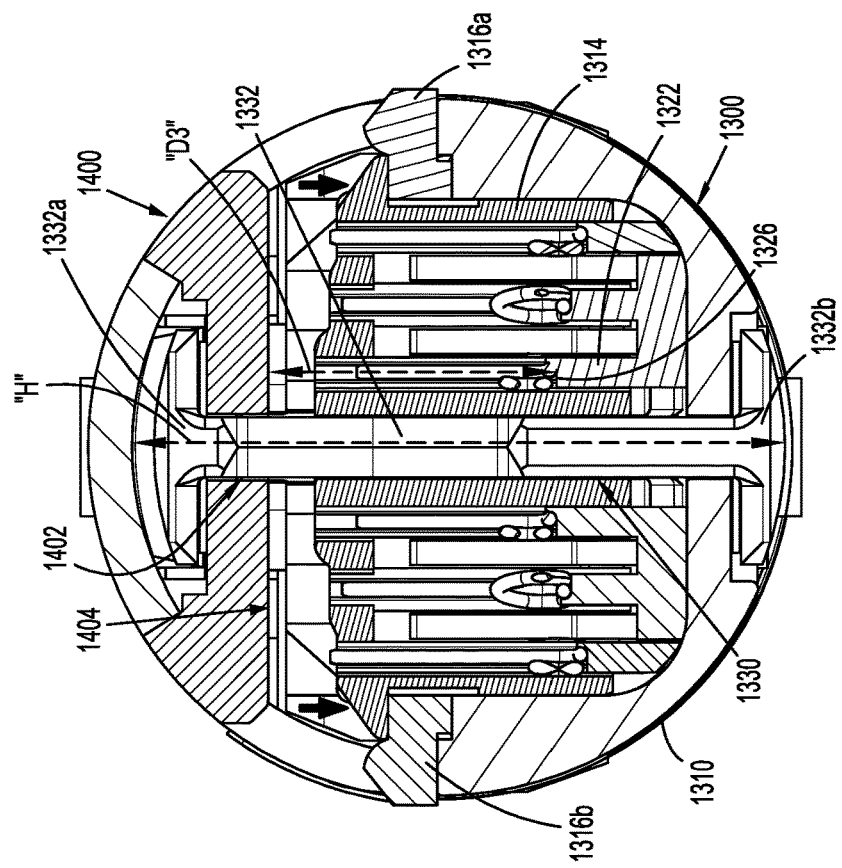
FIG. 16 is a cross-sectional view taken along section lines "16-16" of FIG. 7 with tissue having a second thickness clamped within the tool assembly of the loading unit.
Figure 15:
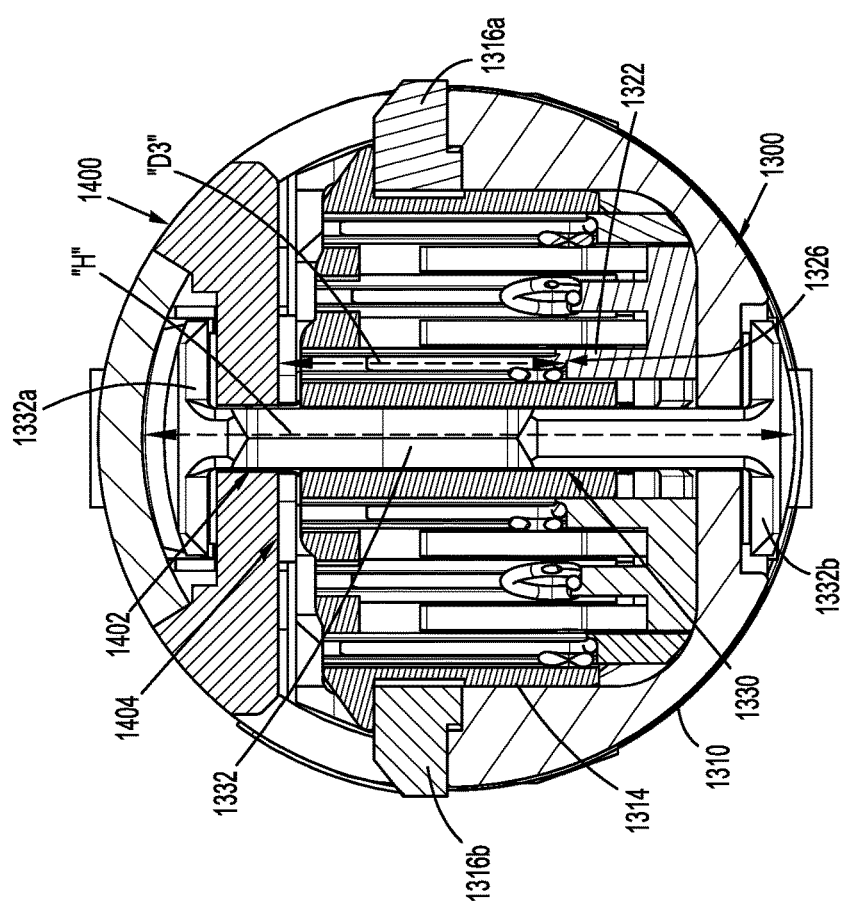
FIG. 15 is a cross-sectional view taken along section lines "15-15" of FIG. 7 with tissue having a first thickness clamped within the tool assembly of the loading unit.

With reference to FIGS. 12-14, each of the plurality of staple seats 1326 of the plurality of pushers 1322 is adapted for releasably receiving the backspan 12 of the surgical staple 100. The staple seat 1326 of the pusher 1322 is skewingly positioned relative to a longitudinal axis "B-B" of the pusher 1322, as illustrated in FIG. 14. It is envisioned that the skewed configuration of the staple seat 1326 of the pusher 1322 is adapted to align the surgical staple 100 with the skewingly positioned staple pocket 1320 of the staple cartridge 1314, as the surgical staple 100 is ejected through the staple pocket 1320 towards the anvil assembly 1400, as illustrated in FIGS. 10, 15, and 16. Specifically, the staple seat 1326 of the pusher 1322 includes a first wall 1326a projecting from a first portion 1326b of the staple seat 1326 and towards the staple pocket 1320 of the staple cartridge 1314, and a second wall 1326c projecting from a second portion 1326d of the staple seat 1326 and towards the staple pocket 1320 of the staple cartridge 1314. The first and second walls 1326a, 1326c of the staple seat 1326 of the pusher 1322 defines a skewed channel 1328 extending between the first and second portions 1326b, 1326d of the staple seat 1326 of the pusher 1322. The skewed channel 1328 of the staple seat 1326 is skewingly positioned relative to the longitudinal axis "B-B" of the pusher 1322.

When the surgical staple 100 is located on the staple seat 1326 of the pusher 1322, the first wall 1326a of the staple seat 1326 is configured to engage the second portion 20 of the backspan 12 and the second wall 1326b of the staple seat 1326 is configured to engage the third portion 22 of the backspan 12 to releasably receive the backspan 12 of the surgical staple 100. Since the skewed channel 1328 of the staple seat 1326 is skewingly positioned relative to the longitudinal axis "B-B" of the pusher 1322, it is envisioned that when the surgical staple 100 is located on the staple seat 1326 of the pusher 1322, the surgical staple 100 is skewingly positioned relative to the longitudinal axis "B-B" of the pusher 1322, as illustrated in FIGS. 13 and 14.

Turning now to FIGS. 8, 9, 15, and 16, in embodiments, the plurality of staple pockets 1320 are arranged in rows on lateral sides of a knife slot 1330 extending through the staple cartridge 1314 of the staple cartridge assembly 1300. The knife slot 1330 is configured to accommodate movement of a knife 1332, or other such cutting element to sever the tissue "T" (see FIGS. 4A-4C) disposed between the staple cartridge assembly 1300 and the anvil assembly 1400. In embodiments, the knife slot 1330 may extend along a centerline "CL" of the staple cartridge 314 of the staple cartridge assembly 1300, as illustrated in FIG. 8. Alternatively, the knife slot 1330 may be laterally offset from the centerline "CL" of the staple cartridge 1314 of the staple cartridge assembly 1300.

With reference to FIGS. 15 and 16, the anvil assembly 1400 includes a corresponding knife slot 1402 on a tissue-facing surface 1404 of the anvil assembly 1400 that is configured to accommodate movement of the knife 1332. In embodiments, the knife 1332 includes an I-beam configuration such that a top portion 1332a of the knife 1332 is movably disposed within the knife slot 1402 of the anvil assembly 1400 and a bottom portion 1332b of the knife 1332 is movably disposed within the knife slot 1330 of the staple cartridge 1314 of the staple cartridge assembly 1300. In any of the embodiments disclosed herein, the knife can have other shapes, or could be part of or attached to the sled.

With continued reference to FIGS. 15 and 16, the knife 1332 includes a height "H". When the staple cartridge assembly 1300 and the anvil assembly 1400 are approximated and the knife 1332 is translated through the respective knife slots 1330, 1402, the height "H" of the knife 1332 provides for a constant distance "D3" between the anvil assembly 1400 and each of the plurality of staple seats 1326 of the plurality of pushers 1322, regardless of the thickness of the tissue "T" (see FIGS. 4A-4C) disposed between the staple cartridge assembly 1300 and the anvil assembly 1400 and regardless of the positioning of the staple cartridge 1314. The height "H" of the knife 1332 also provides for a maximum tissue gap when the knife 1332 is translated through the respective knife slots 1330, 1402.

Referring now to FIGS. 5-16, in operation, the surgical stapling instrument 1000 is manipulated such that the tissue "T" is disposed between the staple cartridge assembly 1300 and the anvil assembly 1400 with the tool assembly 1200 spaced-apart, in the open configuration (see FIG. 6). The staple cartridge assembly 1300 and the anvil assembly 1400 are then approximated by actuating the movable handle 1003A of the handle assembly 1002 to clamp the tissue "T" disposed between the staple cartridge assembly 1300 and the anvil assembly 1400 such that a compressive force is applied to the tissue "T".

With the tissue "T" securely clamped between the staple cartridge assembly 1300 and the anvil assembly 1400, the surgical stapling instrument 1000 is then fired to eject the plurality of surgical staples 100 by actuating the movable handle 1003A. Upon firing the surgical stapling instrument 1000, the actuation sled 1324 (FIG. 8) advances along the elongated support channel 1312 of the carrier 1310 to sequentially contact the plurality of pushers 1322, such that the plurality of pushers 1322 are displaced within the plurality of staple pockets 1320 to eject the plurality of surgical staples 100 from the plurality of staple pockets 1320 towards the anvil assembly 1400.

The plurality of surgical staples 100 pass through the plurality of staple pockets 1320 of the staple cartridge 1314 (see FIG. 8) and through the tissue "T". After passing through the tissue "T," the plurality of surgical staples 100 engage the tissue-facing surface 1404 of the anvil assembly 1400 and are deformed into the substantially B-staple configuration (see FIGS. 4A-4C). Upon formation within the tissue "T," the plurality of surgical staples 100 maintain a compressive force on the tissue "T" to effect hemostasis.

Sequential firing of the surgical staples 100 continues until the actuation sled 1324 is advanced to a distal end of the staple cartridge 1314, at which time all of the plurality of surgical staples 100 housed the staple cartridge 1314 will have been ejected. The knife 1332 may then be translated through the tool assembly 1200 to form an incision between the rows of stapled tissue "T".

Turning now to FIGS. 17A-17D, an exemplary embodiment of a surgical staple in accordance with another aspect of the present disclosure is shown generally as surgical staple 200. The surgical staple 200 is substantially similar to the surgical staple 100 disclosed above (see FIGS. 1-4C) and will therefore be described only to the extent necessary to highlight the differences.

As shown in FIG. 17A, the surgical staple 200 includes a body 210 having a backspan 212, a first leg 214, and a second leg 216. Each of the first and second legs 214, 216 includes a first end portion 214a, 216a, respectively, and a second end portion 214b, 216b, respectively. Each of the second end portions 214b, 216b of the first and second legs 214, 216 includes a tissue-penetrating tip 214c, 216c. The surgical staple 200 has an unformed configuration, as shown in FIGS. 17A, wherein the first leg 214 and the second leg 216 are parallel, or substantially parallel, to one another and spaced a distance from one another. Alternatively, in the unformed configuration, the first and second legs 214, 216 can diverge slightly or converge slightly, etc. in relation to each other.

The backspan 212 includes a first portion 212a including a looped member 218, a second portion 212b that is substantially linear and extends between the first end portion 214a of the first leg 214 and a first end portion 218a of the looped member 218, and a third portion 212c that is substantially linear and extends between the first end portion 216a of the second leg 216 and a second end portion 218b of the looped member 218.

With reference to FIGS. 17A and 17C, in embodiments, the second and third portions 212b, 212c of the backspan 212 defines a crimped region 220 disposed between the first end portion 214a of the first leg 214 and the first end portion 216a of the second leg 216. In embodiments, the crimped region 220 includes a first crimped section 220a formed on the second portion 212b of the backspan 212 and a second crimped section 220b formed on the third portion 212c of the backspan 212. In embodiments, the first crimped section 220a overlaps or is axially aligned with the second crimped section 220b. Alternatively, it is contemplated that the crimped region 220 may be defined by a crimped section in only one of the second and third portions 212b, 212c of the backspan 212. In the crimped region 220, the second and/or the third portions 212b, 212c of the backspan 212 are flattened such that a combined wire thickness "WT" of the first and second crimped sections 220a, 220b of the backspan 212 is approximately equal to a diameter "BD2" of the body 210 of the surgical staple 200. In embodiments, the crimped region 220 of the backspan 212 may be formed by compressing the surgical staple 200 between two substantially flat surfaces via any suitable means.

With additional reference to FIG. 17B, forming the crimped region 220 in the surgical staple 200 aligns an axis "X5-X5" of the second portion 212b with an axis "X6-X6" of the third portion 212c. Further, forming the crimped region 220 in the surgical staple 200 aligns an axis "X7-X7" of the first portion 212a with the axis "X5-X5" and the axis "X6-X6" of the second and third portions 212b, 212c of the backspan 212, respectively. As a result, the first leg 214 of the surgical staple 200 is axially aligned with the second leg 216 of the surgical staple 200 such that the surgical staple 200 is provided with a slim profile as shown in FIG. 17D.

Figure 18:
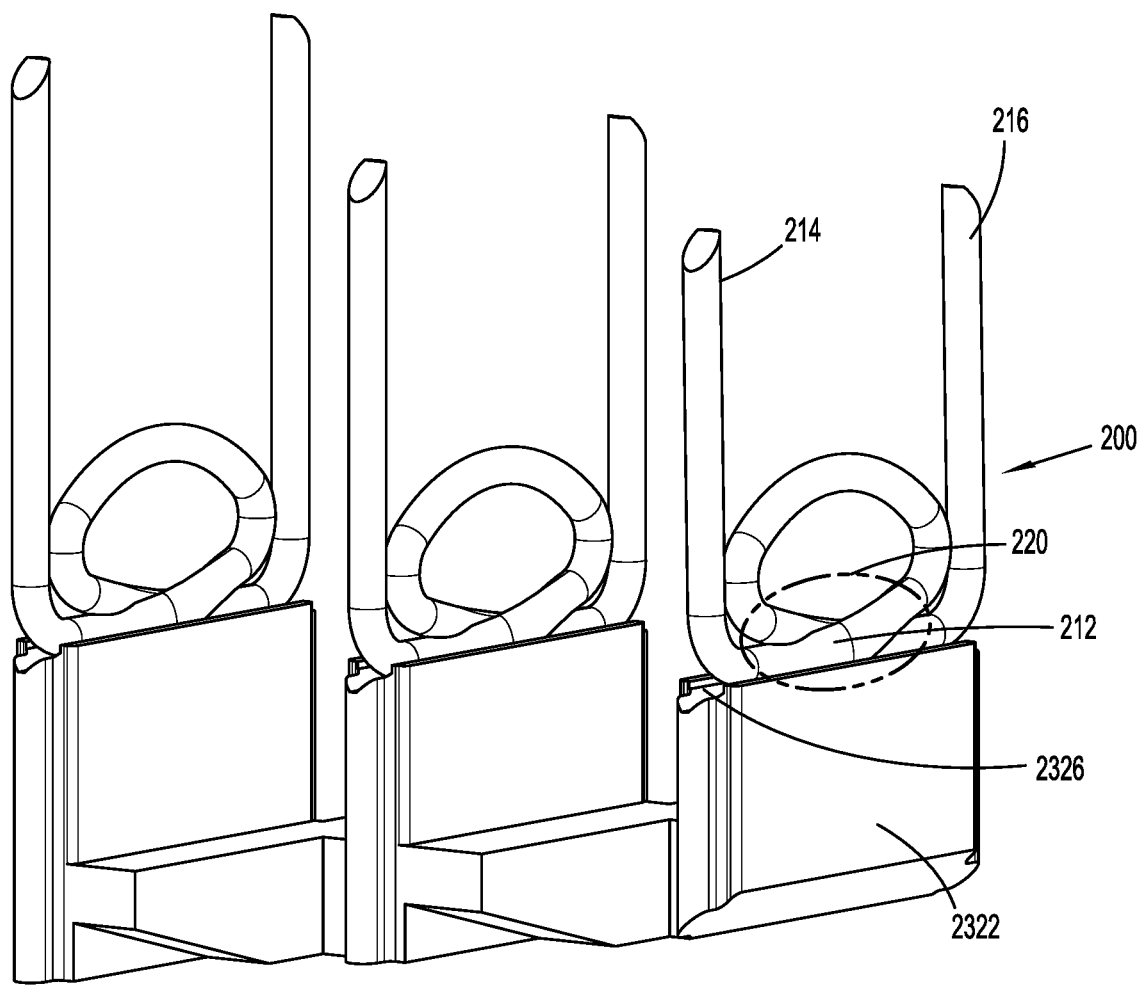
FIG. 18 is a side, perspective view of a pusher of a staple cartridge assembly in accordance with an aspect of the present disclosure that supports the surgical staples of FIG. 17A.

In embodiments, the surgical staple 200 may be used with a known surgical stapling instrument, such as, for example, the surgical stapling instrument disclosed in U.S. Pat. No. 5,865,361, the entire content of which was previously incorporated herein by reference. With reference to FIG. 18, the surgical stapling instrument disclosed in the '361 patent may include conventional pushers such as, for example, a plurality of pushers 2322. In contrast to the skewed configuration of the plurality of pushers 1322 described above (see FIG. 13), each of the plurality of pushers 2322 includes staple seats 2326 that are linear and configured to support the crimped region 220 of a respective surgical staple 200. The slim profile of the surgical staple 200 (see FIG. 17D) also enables the surgical staple 200 to be received through conventional retention slots of a staple cartridge as disclosed in the '361 patent. Thus, it is contemplated that the surgical staple 200 may be used interchangeably with a conventional surgical staple without requiring modifications to the plurality of pushers 2322 or the staple cartridge as disclosed in the '361 patent.

Referring also to FIGS. 4A-4C, as discussed above in regard to the surgical staple 100, the surgical staple 200 may be positioned adjacent the tissue "T" while in an unformed configuration, and then deformed or fastened onto the tissue such that the surgical staple 200, in a formed configuration, defines a substantially B-shaped staple configuration. In order to place the surgical staple 200 in the tissue "T," a surgical apparatus similar to the surgical stapling instrument 1000 (see FIG. 5) disclosed above, and the surgical stapling instrument disclosed in the '361 patent may be used.

Figure 19A:
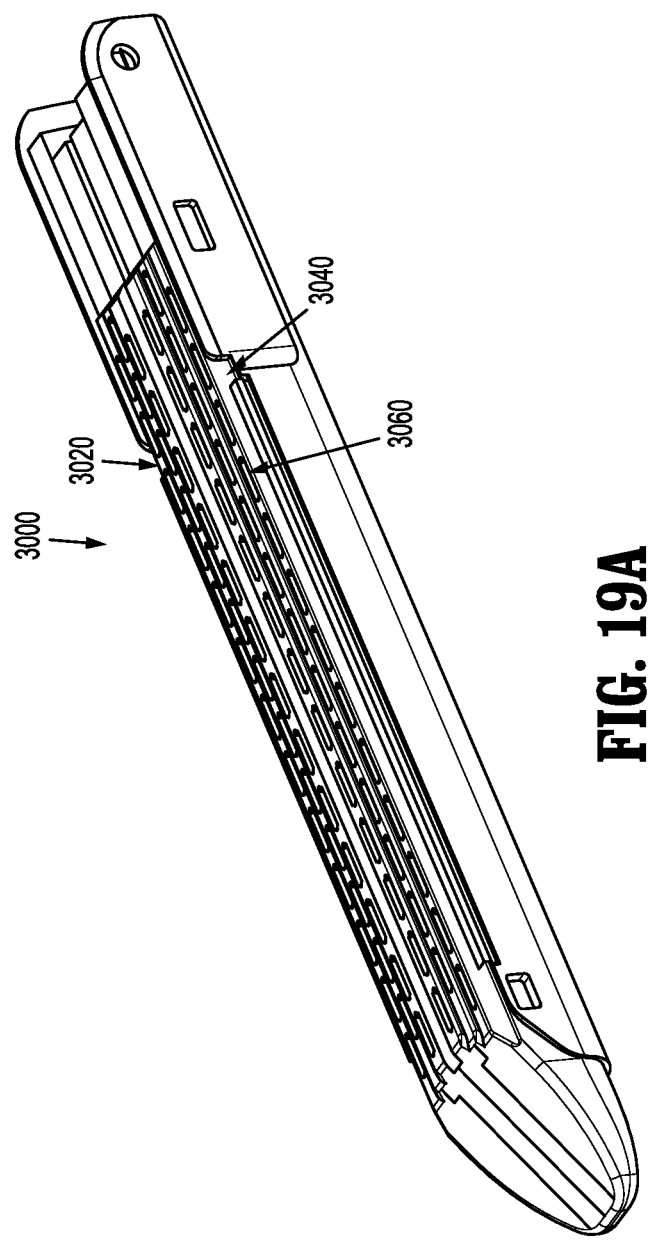
FIG. 19A is a side, perspective view of a staple cartridge assembly in accordance with another aspect of the present disclosure that supports the surgical staples of FIG. 17A.
Figure 19B:
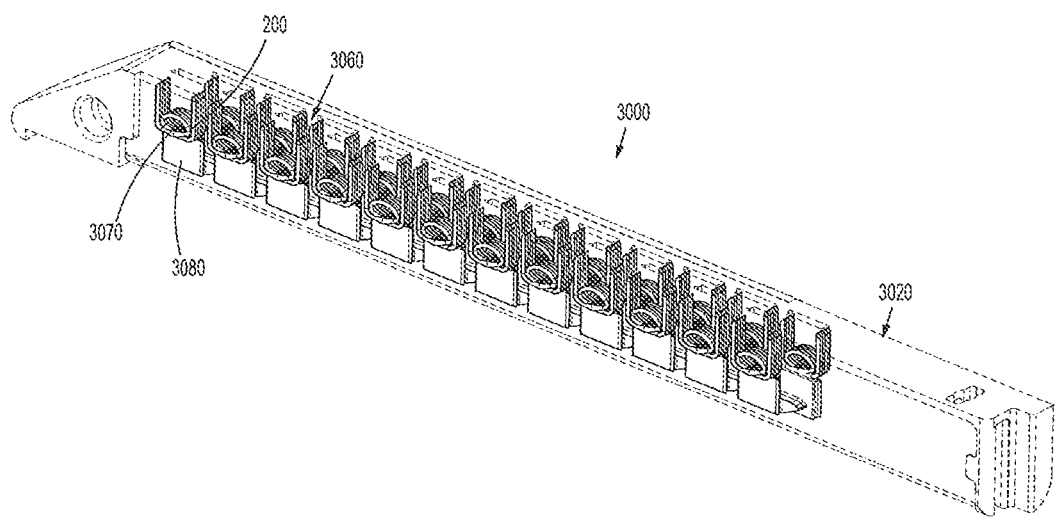
FIG. 19B is a side, perspective view of a staple cartridge of the staple cartridge assembly of FIG. 19A.

With reference to FIGS. 19A and 19B, the slim profile (see FIG. 17D) of the surgical staple 200 also enables a plurality of surgical staples 200 to be disposed in a stacked orientation, and provided for use with a cartridge assembly 3000 similar to the In-Situ Loaded cartridge assembly disclosed in U.S. Pat. No. 9,364,217, the entire content of which is incorporated herein by reference.

The cartridge assembly 3000 generally includes a first staple cartridge 3020, a second staple cartridge 3040, and a plurality of staple pockets 3060 associated with each of the first and second staple cartridges 3020, 3040. Although FIG. 19B only illustrates the first staple cartridge 3020, each of the first and second staple cartridges 3020, 3040 includes a plurality of staple magazines 3070 and a plurality of pushers 3080 operatively associated with the plurality of staple pockets 3060. Each of the plurality of staple magazines 3070 is configured to receive the plurality of surgical staples 200 such that the plurality of surgical staples 200 is disposed therein in the stacked orientation. Once the plurality of surgical staples 200 is loaded into the plurality of staple magazines 3070, the plurality of pushers 3080 is configured to urge the plurality of surgical staples 200 out through the plurality of staple pockets 3060 as disclosed in '217 patent. It is contemplated that the plurality of surgical staples 200 may be used interchangeably with a plurality of conventional staples as disclosed in the '217 patent without requiring modifications to the cartridge assembly 3000.

In any of the embodiments disclosed herein, the tool assembly can be incorporated with the elongate portion of the handle assembly. The staple cartridge can be a removable and replaceable assembly, in an instrument with a replaceable loading unit or tool assembly or incorporated tool assembly.

The surgical staples described herein can be utilized in a configuration where the backspan is not intended to be deformed. In certain embodiments, the backspan can be configured to house a material or object, with a deformable backspan or a backspan that is not deformable. The material or object can include medically useful materials such as a hemostat or sealant, pharmaceuticals such as chemotherapy agents, and even radio-active agents such as brachytherapy particles or seeds. Such materials or objects can be disposed in the opening formed by the looped member or incorporated in a mesh, woven, braided, non-woven material, or a suture, that is disposed in the looped member.

It will be understood that various modifications may be made to the embodiments disclosed herein. For example, the above described staple may be formed from any of a variety of surgically acceptable materials including titanium, plastics, resorbable materials, etc. Therefore, the above description should not be construed as limiting, but merely as exemplifications of preferred embodiments. Those skilled in the art will envision other modifications within the scope and spirit of the claims appended hereto.

What is claimed is:

1. A surgical staple comprising:
    a body having a diameter, the body including:
        a first leg having a first end portion and a second end portion;
        a second leg having a first end portion and a second end portion; and
        a backspan including:
            a first portion having a looped member, the looped member including a first end portion and a second end portion;
            a second portion extending between the first end portion of the first leg and the first end portion of the looped member;
            a third portion extending between the first end portion of the second leg and the second end portion of the looped member; and
            a crimped region including a crimped section defined in at least one of the second portion and the third portion of the backspan, wherein a combined wire thickness of the second and third portions of the backspan in the crimped region is about equal to the diameter of the body of the surgical staple.

2. The surgical staple according to claim 1, wherein the crimped region includes a first crimped section defined on the second portion of the backspan and a second crimped section defined on the third portion of the backspan, wherein the combined wire thickness of the crimped region is about equal to the diameter of the body of the surgical staple.

3. The surgical staple according to claim 2, wherein the first crimped section of the second portion of the backspan overlaps with the second crimped section of the third portion of the backspan.

4. The surgical staple according to claim 3, wherein the looped member of the backspan defines a first axis that extends between the first end portion of the looped member and the second end portion of the looped member.

5. The surgical staple according to claim 4, wherein the second portion of the backspan defines a second axis and the third portion of the backspan defines a third axis, the first axis of the looped member being parallel with the second axis of the second portion and the third axis of the third portion.

6. The surgical staple according to claim 5, wherein the second axis of the second portion of the backspan is laterally aligned with the third axis of the third portion of the backspan such that the first leg and the second leg of the surgical staple are axially aligned.

7. The surgical staple according to claim 5, wherein the looped member of the backspan includes an apex, the second portion of the backspan includes a first mid-portion, and the third portion of the backspan includes a second mid-portion, the apex of the looped member and the first and second mid-portions of the second and third portions of the backspan defining an axis that is perpendicular to the second axis of the second portion of the backspan and the third axis of the third portion of the backspan.

8. The surgical staple according to claim 2, wherein the first crimped section of the second portion of the backspan is axially aligned with the second crimped section of the third portion of the backspan.

9. The surgical staple according to claim 1, wherein the surgical staple includes an unformed configuration and a formed configuration, wherein in the unformed configuration of the surgical staple, the apex of the looped member of the backspan is spaced apart from each of the second and third portions of the backspan a first distance, and wherein in the formed configuration of the surgical staple, the apex of the looped member of the backspan is spaced apart from each of the second and third portions of the backspan a second distance less than the first distance.

10. The surgical staple according to claim 9, wherein the backspan of the surgical staple is positioned to engage tissue such that the second distance between the apex of the looped member of the backspan and each of the second and third portions of the backspan decreases as a thickness of tissue engaged by the backspan increases.

11. The surgical staple according to claim 9, wherein in the formed configuration of the surgical staple, the first leg of the surgical staple is positioned on a first lateral side of the looped member and the second leg of the surgical staple is positioned on a second lateral side of the looped member opposite the first lateral side of the looped member.

12. A surgical staple comprising:
    a body including:
        a first leg having a first end portion and a second end portion;
        a second leg having a first end portion and a second end portion; and
        a backspan including:
            a first portion including a first end portion and a second end portion;
            a second portion extending longitudinally between the first end portion of the first leg and the first end portion of the first portion, the second portion defining a first axis;
            a third portion extending longitudinally between the first end portion of the second leg and the second end portion of the first portion, the third portion defining a second axis; and
            a crimped region including a crimped section defined in at least one of the second portion or the third portion of the backspan, wherein the crimped region aligns the first axis of the second portion with the second axis of the third portion.

13. The surgical staple according to claim 12, wherein the first portion includes a looped member positioned between the first end portion and the second end portion of the first portion.

14. The surgical staple according to claim 13, wherein the looped member of the first portion of the backspan defines a third axis that is parallel with the first axis of the second portion of the backspan and the second axis of the third portion of the backspan.

15. The surgical staple according to claim 12, wherein in the crimped region, the second and third portions of the backspan include a combined wire thickness about equal to a diameter of the body of the surgical staple.

16. The surgical staple according to claim 12, wherein the crimped section defined in the at least one of the second or third portions of the backspan axially aligns the first end portion of the first leg with the first end portion of the second leg.

17. The surgical staple according to claim 12, wherein the crimped region of the backspan is disposed between the first end portion of the first leg and the first end portion of the second leg.

18. The surgical staple according to claim 12, wherein the crimped region includes a first crimped section defined on the second portion of the backspan and a second crimped section defined on the third portion of the backspan.

19. The surgical staple according to claim 18, wherein the first crimped section of the second portion overlaps with the second crimped section of the third portion.

20. The surgical staple according to claim 18, wherein the first crimped section of the second portion is axially aligned with the second crimped section of the third portion, and wherein the second and third portions of the backspan are in lateral contact.

\* \* \* \* \*